(12) United States Patent
Persons et al.

(10) Patent No.: US 6,936,614 B2
(45) Date of Patent: *Aug. 30, 2005

(54) PIPERIDINE-PIPERAZINE LIGANDS FOR NEUROTRANSMITTER RECEPTORS

(75) Inventors: Paul E. Persons, Westborough, MA (US); Heike Radeke, South Grafton, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/808,252

(22) Filed: Mar. 24, 2004

(65) Prior Publication Data

US 2004/0254195 A1 Dec. 16, 2004

Related U.S. Application Data

(63) Continuation of application No. 10/087,609, filed on Mar. 1, 2002, now Pat. No. 6,713,479.
(60) Provisional application No. 60/272,966, filed on Mar. 2, 2001.

(51) Int. Cl.$^7$ ................... A61K 31/495; C07D 401/06
(52) U.S. Cl. ........................ 514/253.01; 514/253.13; 544/360
(58) Field of Search .................. 544/360; 514/253.01, 514/253.13

(56) References Cited

U.S. PATENT DOCUMENTS

| | | | |
|---|---|---|---|
| 4,873,331 A | 10/1989 | Childers, Jr. et al. | 544/295 |
| 5,643,927 A | 7/1997 | Foguet et al. | 514/320 |
| 5,665,725 A | 9/1997 | Moltzen et al. | 514/278 |
| 5,807,871 A | 9/1998 | Moltzen et al. | 514/323 |
| 5,859,246 A | 1/1999 | Thurkauf et al. | 544/392 |
| 5,965,575 A | 10/1999 | Peglion et al. | 514/321 |
| 6,031,099 A | 2/2000 | Moltzen et al. | 546/17 |
| 6,084,098 A | 7/2000 | Kover et al. | 544/373 |
| 6,172,229 B1 | 1/2001 | Thurkauf et al. | 544/392 |
| 6,207,677 B1 | 3/2001 | Moltzen et al. | 514/304 |
| 6,239,126 B1 | 5/2001 | Kelly et al. | 514/211 |
| 6,239,135 B1 | 5/2001 | Kohlman et al. | 514/255.03 |
| 6,251,893 B1 | 6/2001 | Maddaford et al. | 514/214.01 |
| 6,255,302 B1 | 7/2001 | Kelly et al. | 514/217.05 |
| 6,284,759 B1 | 9/2001 | He | 514/252.19 |
| 6,316,470 B1 | 11/2001 | Kover et al. | 514/323 |
| 6,333,339 B1 | 12/2001 | Boerttcher et al. | 514/323 |
| 6,358,958 B2 | 3/2002 | Kohlman et al. | 514/255.03 |
| 6,376,494 B1 | 4/2002 | Childers et al. | 514/252.14 |
| 6,713,479 B2 * | 3/2004 | Persons et al. | 514/253.01 |

FOREIGN PATENT DOCUMENTS

| | | |
|---|---|---|
| WO | WO 95/25733 | 9/1995 |
| WO | WO 98/57953 | 12/1998 |
| WO | WO 99/65906 | 12/1999 |

OTHER PUBLICATIONS

International Search Report Completed on Jun. 29, 2002 and Mailed on Aug. 8, 2002.
Basic & Clinical Pharmacology, (6$^{th}$. Ed.) by Appleton & Lange, pp. 132–141 (1995).
Van Tol, et al., "Cloning Of The Gene For A Human Dopamine D4 Receptor With High Affinity For The Antipsychotic Clozapine", Nature, vol. 350, pp. 610–614 (1991).
Robichaud, A.J., et al., "Recent Advances in Selective Serotonin Receptor Modulation", Annual Reports in Medicinal Chemistry, vol. 35, pp. 11–20 (2000).

* cited by examiner

Primary Examiner—Richard L. Raymond
(74) Attorney, Agent, or Firm—Dana M. Gordon; Foley Hoag LLP

(57) ABSTRACT

One aspect of the present invention relates to piperidine-piperazine compounds. A second aspect of the present invention relates to the use of the piperidine-piperazine compounds as ligands for various mammalian cellular receptors or transporters or both, including dopamine, serotonin or norepinephrine receptors or transporters, any combination of them, or all of them. The compounds of the present invention will find use in the treatment of numerous ailments, conditions and diseases which afflict mammals, including but not limited to addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome. An additional aspect of the present invention relates to the synthesis of combinatorial libraries of the piperidine-piperazine compounds, and the screening of those libraries for biological activity, e.g., in assays based on dopamine receptors or transporters or both.

20 Claims, 6 Drawing Sheets

Figure 1
*Radioligand binding results ($IC_{50}$ values)
for certain compounds of the present invention*
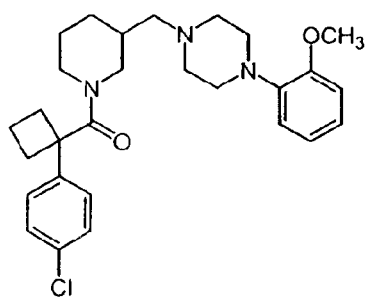 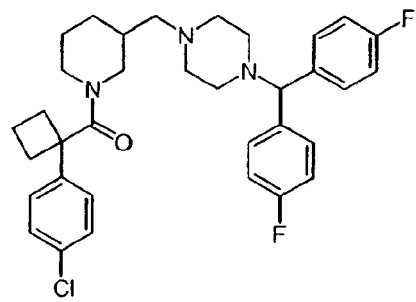
3
$IC_{50}$ values
$D_{2L}$ (human) < 500 nM
$D_{4.4}$ (human) > 1 μM
$5HT_{1A}$ (human) < 500 nM
$5HT_{2A}$ (human) < 100 nM
$5HT_{2B}$ (human) < 100 nM
$5HT_{2C}$ (human) < 100 nM
$alpha_{1A}$ (rat) < 100 nM
$alpha_{1D}$ (human) < 100 nM
$alpha_{2A}$ (human) < 1 μM
4
$IC_{50}$ values
$D_{2L}$ (human) < 500 nM
$5HT_{2A}$ (human) < 100 nM
$5HT_{2B}$ (human) < 10 nM
$5HT_{2C}$ (human) < 500 nM

*Radioligand binding results (IC$_{50}$ values) for certain compounds of the present invention*

5
IC$_{50}$ values
D$_{2L}$ (human) < 5 μM
5HT$_{2A}$ (human) < 10 nM
5HT$_{2B}$ (human) < 10 nM
5HT$_{2C}$ (human) < 10 nM

6
IC$_{50}$ values
D$_{2L}$ (human) < 5 μM
5HT$_{2A}$ (human) < 10 nM
5HT$_{2B}$ (human) < 100 nM
5HT$_{2C}$ (human) < 10 nM Figure 3
*Radioligand binding results ($IC_{50}$ values)
for certain compounds of the present invention*
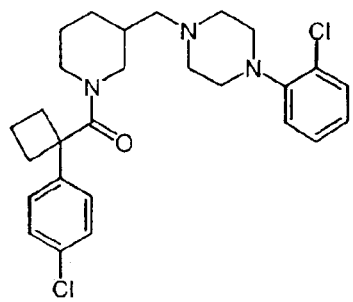 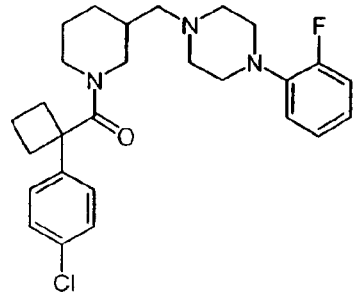
| 7 | 8 |
|---|---|
| $IC_{50}$ values | $IC_{50}$ values |
| $D_{2L}$ (human) > 1 μM | $D_{2L}$ (human) < 1 μM |
| $D_3$ (human) < 1 μM | $D_3$ (human) < 1 μM |
| $5HT_1$ (rat) > 1 μM | $5HT_1$ (rat) > 1 μM |
| $5HT_{1A}$ (human) < 500 nM | $5HT_{1A}$ (human) < 1 μM |
| $5HT_2$ (rat) < 100 nM | $5HT_2$ (rat) < 100 nM |
| $5HT_{2A}$ (human) < 10 nM | $5HT_{2A}$ (human) < 10 nM |
| $5HT_{2B}$ (human) < 100 nM | $5HT_{2B}$ (human) < 100 nM |
| $5HT_{2C}$ (human) < 100 nM | $5HT_{2C}$ (human) < 10 nM |

Figure 4

*Radioligand binding results ($IC_{50}$ values)
for certain compounds of the present invention*

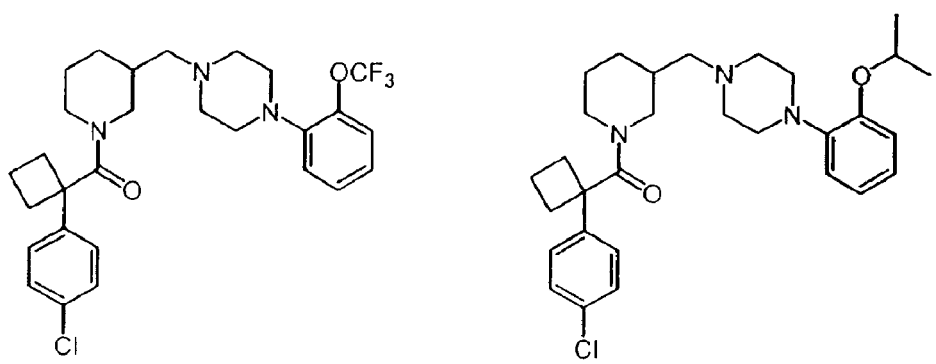

9
$IC_{50}$ values
$D_{2L}$ (human) < 1 μM
$D_3$ (human) < 500 nM
$D_{4.4}$ (human) > 1 μM
$5HT_{1A}$ (human) < 500 nM
$5HT_{2A}$ (human) < 500 nM
$5HT_{2B}$ (human) < 100 nM
$5HT_{2C}$ (human) < 500 nM
$5HT_6$ (human) > 1 μM
$alpha_{1A}$ (rat) < 1 μM
$alpha_{1D}$ (human) > 1 μM
$alpha_{2A}$ (human) > 1 μM 11
$IC_{50}$ values
$D_{2L}$ (human) < 1 μM
$D_{2S}$ (human) < 1 μM
$D_3$ (human) < 1 μM
$D_{4.4}$ (human) > 1 μM
$5HT_2$ (rat) > 1 μM
$5HT_3$ (human) > 1 μM
$5HT_6$ (human) > 1 μM
$5HT_7$ (human) < 1 μM Figure 5
*Radioligand binding results ($IC_{50}$ values) for certain compounds of the present invention*
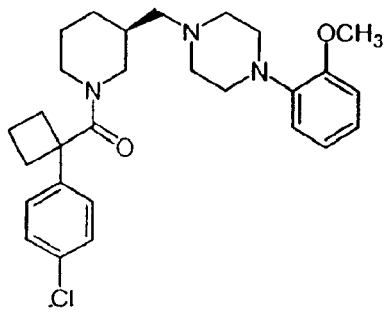
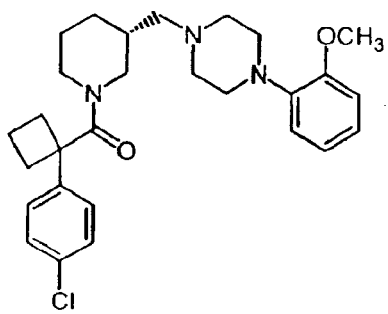
13
$IC_{50}$ values
$D_{2L}$ (human) < 500 nM
$5HT_{2A}$ (human) < 100 nM
$5HT_{2B}$ (human) < 100 nM
$5HT_{2C}$ (human) < 500 nM
$alpha_{1A}$ (rat) > 1 µM
$alpha_{1D}$ (human) < 500 nM
$alpha_{2A}$ (human) < 1 µM
14
$IC_{50}$ values
$D_{2L}$ (human) < 500 nM
$5HT_{2A}$ (human) < 500 nM
$5HT_{2B}$ (human) < 100 nM
$5HT_{2C}$ (human) < 500 nM
$alpha_{1A}$ (rat) < 100 nM
$alpha_{1D}$ (human) < 100 nM
$alpha_{2A}$ (human) < 1 µM

*Radioligand binding results ($IC_{50}$ values) for certain compounds of the present invention*

15
$IC_{50}$ values
NE Transporter (human) <500 nM
$D_{2L}$ (human) <500 nM
$D_3$ (human) <500 nM
DA Transporter (human) <100 nM
5-$HT_7$ (human) <500 nM
5-HT Transporter (human) >1 µM

16
$IC_{50}$ values
alpha 1 (rat) <1 µM
alpha 2 (rat) <1 µM
$D_{2L}$ (human) <1 µM
$D_{2S}$ (human) >1 µM
$D_3$ (human) <1 µM
$D_{4.4}$ (human) >1 µM
5-$HT_7$ (human) <1 µM
5-$HT_{2A}$ (human) <1 µM

PIPERIDINE-PIPERAZINE LIGANDS FOR NEUROTRANSMITTER RECEPTORS

RELATED APPLICATIONS

This application is a continuation of U.S. patent application Ser. No. 10/087,609, filed Mar. 1, 2002, now U.S. Pat. No. 6,713,479; which claims the benefit of priority under 35 USC § 119(e) to U.S. Provisional Patent Application Ser. No. 60/272,966, filed Mar. 2, 2001.

BACKGROUND OF THE INVENTION

Dopamine, norepinephrine and serotonin are mammalian monoamine neurotransmitters that play important roles in a wide variety of physiological processes. Therefore, compounds that selectively modulate the activity of these three neurotransmitters, either individually, in pairs, or as a group, promise to serve as agents effective in the treatment of a wide range of maladies, conditions and diseases that afflict mammals due to atypical activities of these neurotransmitters.

For example, depression and psychosis are believed to result from dysfunction in the noradrenergic or serotonergic systems. Furthermore, the noradrenergic system appears to be associated with increased drive, whereas the serotonergic system relates more to changes in mood. Therefore, it is possible that the different symptoms of depression may benefit from drugs acting mainly on one or the other of these neurotransmitter systems. On the other hand, a single compound that selectively affects both the noradrenergic and serotonergic systems should prove effective in the treatment of depression comprising symptoms related to dysfunction in both systems.

Dopamine plays a major role in addiction and psychosis. Many of the concepts that apply to dopamine apply to other neurotransmitters as well. As a chemical messenger, dopamine is similar to adrenaline. Dopamine affects brain processes that control movement, emotional response, and ability to experience pleasure and pain. Regulation of dopamine plays a crucial role in our mental and physical health. Neurons containing the neurotransmitter dopamine are clustered in the midbrain in an area called the substantia nigra. In Parkinson's disease, the dopamine-transmitting neurons in this area die. As a result, the brains of people with Parkinson's disease contain almost no dopamine. To help relieve their symptoms, these patients are given L-DOPA, a drug that can be converted in the brain to dopamine.

Certain drugs are known as dopamine agonists. These drugs bind to dopamine receptors in place of dopamine and directly stimulate those receptors. Some dopamine agonists are currently used to treat Parkinson's disease. These drugs can stimulate dopamine receptors even in someone without dopamine-secreting neurons. In contrast to dopamine agonists, dopamine antagonists are drugs that bind but don't stimulate dopamine receptors. Antagonists can prevent or reverse the actions of dopamine by keeping dopamine from attaching to receptors.

Dopamine antagonists are traditionally used to treat schizophrenia and related mental disorders. A person with schizophrenia may have an overactive dopamine system. Dopamine antagonists can help regulate this system by "turning down" dopamine activity.

Cocaine and other drugs of abuse can alter dopamine function. Such drugs may have very different actions. The specific action depends on which dopamine receptors the drugs stimulate or block, and how well they mimic dopamine. Drugs such as cocaine and amphetamine produce their effects by changing the flow of neurotransmitters. These drugs are defined as indirect acting because they depend on the activity of neurons. In contrast, some drugs bypass neurotransmitters altogether and act directly on receptors. Such drugs are direct acting.

Use of these two types of drugs can lead to very different results in treating the same disease. As mentioned earlier, people with Parkinson's disease lose neurons that contain dopamine. To compensate for this loss, the body produces more dopamine receptors on other neurons. Indirect agonists are not very effective in treating the disease since they depend on the presence of dopamine neurons. In contrast, direct agonists are more effective because they stimulate dopamine receptors even when dopamine neurons are missing.

Certain drugs increase dopamine concentrations by preventing dopamine reuptake, leaving more dopamine in the synapse. An example is the widely abused stimulant drug, cocaine. Another example is methylphenidate, used therapeutically to treat childhood hyperkinesis and symptoms of schizophrenia.

Sensitization or desensitization normally occur with drug exposure. However, addiction or mental illness can tamper with the reuptake system. This disrupts the normal levels of neurotransmitters in the brain and can lead to faulty desensitization or sensitization. If this happens in a region of the brain that serves emotion or motivation, the individual can suffer severe consequences. For example, cocaine prevents dopamine reuptake by binding to proteins that normally transport dopamine. Not only does cocaine "bully" dopamine out of the way, it also hangs on to the transport proteins much longer than dopamine does. As a result, more dopamine remains to stimulate neurons, which causes a prolonged feelings of pleasure and excitement. Amphetamine also increases dopamine levels. Again, the result is over-stimulation of these pleasure-pathway nerves in the brain.

Dopamine activity is implicated in the reinforcing effects of cocaine, amphetamine and natural rewards. However, dopamine abnormalities are also believed to underlie some of the core attention deficits seen in acute schizophrenics.

Norepinephrine, also called noradrenaline, is a neurotransmitter that doubles part-time as a hormone. As a neurotransmitter, norepinephrine helps to regulate arousal, dreaming, and moods. As a hormone, it acts to increase blood pressure, constrict blood vessels and increase heart rate—responses that occur when we feel stress.

Serotonin (5-hydroxytryptamine, 5-HT) is widely distributed in animals and plants, occurring in vertebrates, fruits, nuts, and venoms. A number of congeners of serotonin are also found in nature and have been shown to possess a variety of peripheral and central nervous system activities. Serotonin may be obtained from a variety of dietary sources; however, endogenous 5-HT is synthesized in situ from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA).

Serotonin is implicated in the etiology or treatment of various disorders, particularly those of the central nervous system, including anxiety, depression, obsessive-compulsive disorder, schizophrenia, stroke, obesity, pain, hypertension, vascular disorders, migraine, and nausea. Recently, understanding of the role of 5-HT in these and other disorders has advanced rapidly due to increasing understanding of the physiological role of various serotonin receptor subtypes.

It is currently estimated that up to 30% of clinically diagnosed cases of depression are resistant to all forms of drug therapy. To achieve an effective therapy for such patients, it is logical to develop drugs that possess reuptake inhibition profiles different from those of drugs currently available on the market. For example, the exact role of dopamine in depressive illness is far from clear; however, intervention in the dopamine system may hold promise for the treatment of a subset of major depression.

SUMMARY OF THE INVENTION

One aspect of the present invention relates to piperidine-piperazine compounds. A second aspect of the present invention relates to the use of the piperidine-piperazine compounds as ligands for various mammalian cellular receptors or transporters or both, including dopamine, serotonin and norepinephrine receptors or transporters, any combination of them, or all of them. The compounds of the present invention will find use in the treatment of numerous ailments, conditions and diseases which afflict mammals, including but not limited to addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome. An additional aspect of the present invention relates to the synthesis of combinatorial libraries of the piperidine-piperazine compounds, and the screening of those libraries for biological activity, e.g., in assays based on dopamine receptors or transporters or both.

BRIEF DESCRIPTION OF THE FIGURES

FIG. 1 depicts certain compounds of the present invention and their $IC_{50}$ values in various assays based on human and rat neurotransmitter receptors.

FIG. 3 depicts certain compounds of the present invention and their $IC_{50}$ values in various assays based on human and rat neurotransmitter receptors.

FIG. 4 depicts certain compounds of the present invention and their $IC_{50}$ values in various assays based on human and rat neurotransmitter receptors.

FIG. 5 depicts certain compounds of the present invention and their $IC_{50}$ values in various assays based on human and rat neurotransmitter receptors.

DETAILED DESCRIPTION OF THE INVENTION

Figure 2:
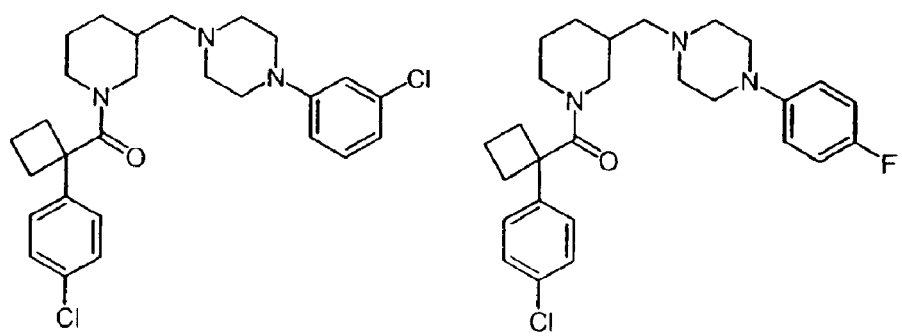
FIG. 2 depicts certain compounds of the present invention and their $IC_{50}$ values in various assays based on human and rat neurotransmitter receptors.
Figure 6:
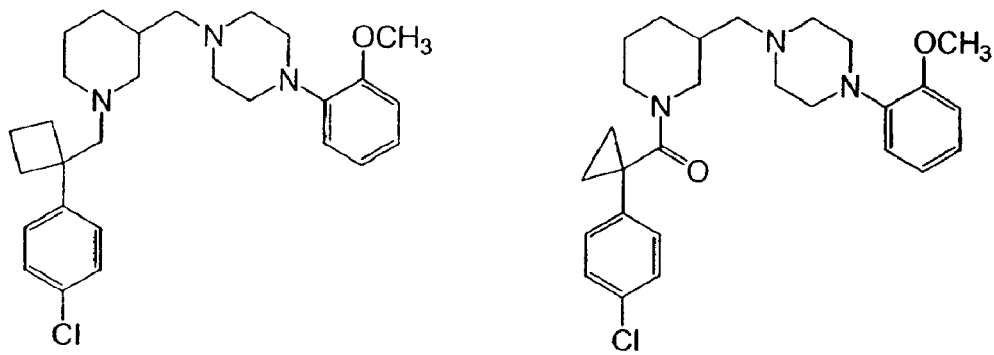
FIG. 6 depicts certain compounds of the present invention and their $IC_{50}$ values in various assays based on human and rat neurotransmitter receptors.

The present invention provides piperidine-piperazine compounds, and combinatorial libraries thereof. Further, the present invention provides piperidine-piperazine compounds that are ligands for dopamine, serotonin or norepinephrine receptors or dopamine, serotonin or norepinephrine transporters, or any combination of them, or all of them. The present invention also relates to methods of using said piperidine-piperazine compounds for the treatment of numerous ailments, conditions and diseases which afflict mammals, including but not limited to addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome. The present invention also relates to pharmaceutical formulations of the piperidine-piperazine compounds.

In certain embodiments, compounds of the present invention are ligands for mammalian receptors or transporters for dopamine, norepinephrine, serotonin, any two of these three neurotransmitters or all of them. In certain embodiments, compounds of the present invention are ligands for mammalian transporters of dopamine, norepinephrine, serotonin, any two of these three neurotransmitters or all of them. In certain embodiments, compounds of the present invention are agonists of mammalian receptors for dopamine, norepinephrine, serotonin, any two of these three neurotransmitters or all of them. In certain embodiments, compounds of the present invention are inverse agonists of mammalian receptors for dopamine, norepinephrine, serotonin, any two of these three neurotransmitters or all of them. In certain embodiments, compounds of the present invention are antagonists of mammalian receptors for dopamine, norepinephrine, serotonin, any two of these three neurotransmitters or all of them. In certain embodiments, compounds of the present invention are agonists of mammalian transporters of dopamine, norepinephrine, serotonin, any two of these three neurotransmitters or all of them. In certain embodiments, compounds of the present invention are antagonists of mammalian transporters of dopamine, norepinephrine, serotonin, any two of these three neurotransmitters or all of them.

In certain embodiments, compounds of the present invention are ligands for mammalian dopamine receptors. In certain embodiments, compounds of the present invention are ligands for mammalian dopamine transporters. In certain embodiments, compounds of the present invention are agonists of mammalian dopamine receptors. In certain embodiments, compounds of the present invention are antagonists of mammalian dopamine receptors. In certain embodiments, compounds of the present invention are agonists of mammalian dopamine transporters. In certain embodiments, compounds of the present invention are antagonists or inverse agonists of mammalian dopamine transporters.

In certain embodiments, compounds of the present invention are ligands for mammalian serotonin receptors. In certain embodiments, compounds of the present invention are ligands for mammalian serotonin transporters. In certain embodiments, compounds of the present invention are agonists of mammalian serotonin receptors. In certain embodiments, compounds of the present invention are antagonists of mammalian serotonin receptors. In certain embodiments, compounds of the present invention are agonists of mammalian serotonin transporters. In certain embodiments, compounds of the present invention are antagonists or inverse agonists of mammalian serotonin transporters.

The mammalian dopamine and serotonin receptors and transporters are members of a family of cell surface proteins that permit intracellular transduction of extracellular signals. Cell surface proteins provide eukaryotic and prokaryotic cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as growth hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milleseconds, such as the opening of ligand-gated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (see, e.g., Sheng et al. (1990) Neuron 4: 477–485), and genes whose expression requires protein synthesis and whose expression is induced or altered over the course of hours.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as neurotransmitters, growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A. G., Ann. Rev. Biochem. 56: 615–649 (1987), Strader, C. D. et al. The FASEB Journal 3: 1825–1832 (1989), Kobilka, B. K., et al. Nature 329:75–79 (1985) and Young et al. Cell 45: 711–719 (1986)). Among the G protein-coupled receptors that have been identified and cloned are the substance P receptor, the angiotensin receptor, the alpha- and beta-adrenergic receptors and the serotonin receptors. G protein-coupled receptors share a conserved structural motif. The general and common structural features of the G protein-coupled receptors are the existence of seven hydrophobic stretches of about 20–25 amino acids each surrounded by eight hydrophilic regions of variable length. It has been postulated that each of the seven hydrophobic regions forms a transmembrane alpha helix and the intervening hydrophilic regions form alternately intracellularly and extracellularly exposed loops. The third cytosolic loop between transmembrane domains five and six is the intracellular domain responsible for the interaction with G proteins.

G protein-coupled receptors are known to be inducible. This inducibility was originally described in lower eukaryotes. For example, the cAMP receptor of the cellular slime mold, Dictyostelium, is induced during differentiation (Klein et al., Science 241: 1467–1472 (1988). During the Dictyostelium discoideum differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235–239 (1989) and Devreotes, P., Science 245: 1054–1058 (1989)).

Definitions

For convenience, certain terms employed in the specification, examples, and appended claims are collected here.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that maybe used to treat specific diseases by modulating the activity of specific cell surface receptors.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "competitive antagonist" refers to a compound that binds to a receptor site; its effects can be overcome by increased concentration of the agonist.

The term "inverse agonist" refers to a compound that binds to a constitutively active receptor site and reduces its physiological function.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

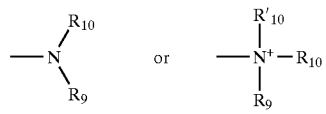

wherein $R_9$, $R_{10}$ and $R'_{10}$ each independently represent a group permitted by the rules of valence.

The term "acylamino" is art-recognized and refers to a moiety that can be represented by the general formula:

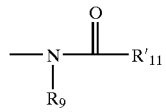

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

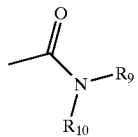

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

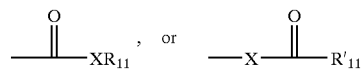

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

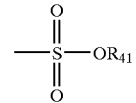

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The term "sulfate" is art recognized and includes a moiety that can be represented by the general formula:

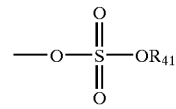

in which $R_{41}$ is as defined above.

The term "sulfonylamino" is art recognized and includes a moiety that can be represented by the general formula:

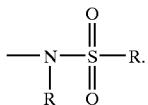

The term "sulfamoyl" is art-recognized and includes a moiety that can be represented by the general formula:

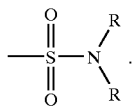

The term "sulfonyl", as used herein, refers to a moiety that can be represented by the general formula:

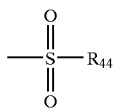

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

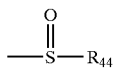

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover.

Compounds of the Invention

In certain embodiments, a compound of the present invention is represented by A:

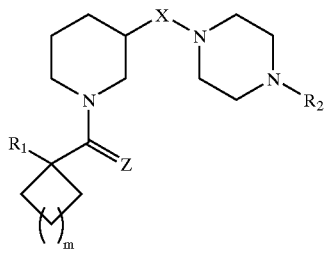

wherein
X represents $(C(R)_2)_n$;
Z represents O or $H_2$;
R represents independently for each occurrence H, alkyl, cycloalkyl, aryl, heteroaryl, aralkyl, or heteroaralkyl; or any two geminal instances of R taken together represent O;
$R_1$ represents optionally substituted aryl or heteroaryl; wherein any optional substituent is selected from the group consisting of alkyl, cycloalkyl, fluoro, chloro, bromo, iodo, hydroxy, alkoxy, acyloxy, acyl, nitro, nitroso, amino, acylamino, sulfonyl, and sulfonylamino;
$R_2$ represents optionally substituted aryl, heteroaryl, arylalkyl, heteroarylalkyl, di(aryl)alkyl, or di(heteroaryl)alkyl; wherein any optional substituent is selected from the group consisting of alkyl, cycloalkyl, fluoro, chloro, bromo, iodo, hydroxy, alkoxy, acyloxy, acyl, nitro, nitroso, amino, acylamino, sulfonyl, and sulfonylamino;
m is 0, 1, 2, or 3;
n is 1, 2, or 3; and
the stereochemical configuration at any stereocenter of a compound represented by A is R, S, or a mixture of these configurations.

In certain embodiments, the compounds of the present invention are represented by A and the attendant definitions, wherein R represents independently for each occurrence H.

In certain embodiments, the compounds of the present invention are represented by A and the attendant definitions, wherein $R_1$ represents optionally substituted phenyl.

In certain embodiments, the compounds of the present invention are represented by A and the attendant definitions, wherein $R_1$ represents 4-chlorophenyl.

In certain embodiments, the compounds of the present invention are represented by A and the attendant definitions, wherein $R_2$ represents optionally substituted phenyl or diphenylmethyl.

In certain embodiments, the compounds of the present invention are represented by A and the attendant definitions, wherein $R_2$ represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl.

In certain embodiments, the compounds of the present invention are represented by A and the attendant definitions, wherein m is 0, 1, or 2.

In certain embodiments, the compounds of the present invention are represented by A and the attendant definitions, wherein n is 1.

In certain embodiments, the compounds of the present invention are represented by A and the attendant definitions, wherein R represents independently for each occurrence H; and $R_1$ represents optionally substituted phenyl.

In certain embodiments, the compounds of the present invention are represented by A and the attendant definitions, wherein R represents independently for each occurrence H; and $R_1$ represents 4-chlorophenyl.

In certain embodiments, the compounds of the present invention are represented by A and the attendant definitions, wherein R represents independently for each occurrence H; and $R_2$ represents optionally substituted phenyl or diphenylmethyl.

In certain embodiments, the compounds of the present invention are represented by A and the attendant definitions, wherein R represents independently for each occurrence H; and $R_2$ represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl.

In certain embodiments, the compounds of the present invention are represented by A and the attendant definitions, wherein R represents independently for each occurrence H; $R_1$ represents optionally substituted phenyl; and $R_2$ represents optionally substituted phenyl or diphenylmethyl.

In certain embodiments, the compounds of the present invention are represented by A and the attendant definitions, wherein R represents independently for each occurrence H; $R_1$ represents 4-chlorophenyl; and $R_2$ represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl) methyl.

In certain embodiments, the compounds of the present invention are represented by A and the attendant definitions, wherein R represents independently for each occurrence H; $R_1$ represents optionally substituted phenyl; $R_2$ represents optionally substituted phenyl or diphenylmethyl; and m is 0, 1, or 2.

In certain embodiments, the compounds of the present invention are represented by A and the attendant definitions, wherein R represents independently for each occurrence H; $R_1$ represents 4-chlorophenyl; $R_2$ represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl) methyl; and m is 0, 1, or 2.

In certain embodiments, the compounds of the present invention are represented by A and the attendant definitions, wherein R represents independently for each occurrence H; $R_1$ represents optionally substituted phenyl; $R_2$ represents optionally substituted phenyl or diphenylmethyl; m is 0, 1, or 2; and n is 1.

In certain embodiments, the compounds of the present invention are represented by A and the attendant definitions, wherein R represents independently for each occurrence H; $R_1$ represents 4-chlorophenyl; $R_2$ represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl) methyl; m is 0, 1, or 2; and n is 1.

In assays based on mammalian dopamine, serotonin, or norepinephrine receptors or transporters, certain compounds according to structure A have $IC_{50}$ values less than 1 µM, more preferably less than 100 nM, and most preferably less than 10 nM.

In assays based on mammalian dopamine receptors or transporters, certain compounds according to structure A have $IC_{50}$ values less than 1 µM, more preferably less than 100 nM, and most preferably less than 10 nM.

In assays based on mammalian serotonin receptors or transporters, certain compounds according to structure A have $IC_{50}$ values less than 1 µM, more preferably less than 100 nM, and most preferably less than 10 nM.

In assays based on mammalian dopamine, serotonin, or norepinephrine receptors or transporters, certain compounds according to structure A have $EC_{50}$ values less than 1 μM, more preferably less than 100 nM, and most preferably less than 10 nM.

In assays based on mammalian dopamine receptors or transporters, certain compounds according to structure A have $EC_{50}$ values less than 1 μM, more preferably less than 100 nM, and most preferably less than 10 nM.

In assays based on mammalian serotonin receptors or transporters, certain compounds according to structure A have $EC_{50}$ values less than 1 μM, more preferably less than 100 nM, and most preferably less than 10 nM.

In certain embodiments, compounds according to structure A are effective in the treatment of mammals suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome.

In certain embodiments, the present invention relates to a compound represented by any of the structures outlined above, wherein said compound is a single stereoisomer.

In certain embodiments, the present invention relates to a formulation, comprising a compound represented by any of the structures outlined above; and a pharmaceutically acceptable excipient.

In certain embodiments, the present invention relates to ligands for receptors or transporters of dopamine, serotonin, or norepinephrine, wherein the ligands are represented by any of the structures outlined above, and any of the sets of definitions associated with one of those structures. In certain embodiments, the ligands of the present invention are antagonists or agonists of receptors or transporters of dopamine, serotonin, or norepinephrine. In any event, the ligands of the present invention preferably exert their effect on the dopamine, serotonin, or norepinephrine receptors or transporters at a concentration less than about 1 micromolar, more preferably at a concentration less than about 100 nanomolar, and most preferably at a concentration less than 10 nanomolar.

In certain embodiments, the selectivity of a ligand for dopamine receptors or transporters renders that ligand an effective therapeutic agent for an acute or chronic ailment, disease or malady. In certain embodiments, the selectivity of a ligand for dopamine receptors or transporters consists of a binding affinity for dopamine receptors or transporters at least a factor of ten greater than its binding affinity for receptors or transporters of other neurotransmitters. In certain embodiments, the selectivity of a ligand for dopamine receptors or transporters consists of a binding affinity for dopamine receptors or transporters at least a factor of one hundred greater than its binding affinity for receptors or transporters of other neurotransmitters. In certain embodiments, the selectivity of a ligand for dopamine receptors or transporters consists of a binding affinity for dopamine receptors or transporters at least a factor of one thousand greater than its binding affinity for receptors or transporters of other neurotransmitters.

In certain embodiments, the selectivity of a ligand for serotonin receptors or transporters renders that ligand an effective therapeutic agent for an acute or chronic ailment, disease or malady. In certain embodiments, the selectivity of a ligand for serotonin receptors or transporters consists of a binding affinity for serotonin receptors or transporters at least a factor of ten greater than its binding affinity for receptors or transporters of other neurotransmitters. In certain embodiments, the selectivity of a ligand for serotonin receptors or transporters consists of a binding affinity for serotonin receptors or transporters at least a factor of one hundred greater than its binding affinity for receptors or transporters of other neurotransmitters. In certain embodiments, the selectivity of a ligand for serotonin receptors or transporters consists of a binding affinity for serotonin receptors or transporters at least a factor of one thousand greater than its binding affinity for receptors or transporters of other neurotransmitters.

The present invention contemplates pharmaceutical formulations of the ligands of the present invention. In certain embodiments, the pharmaceutical formulations will comprise ligands of the present invention that selectively effect serotonin receptors or transporters, and thereby have a therapeutic effect on an acute or chronic ailment, disease or malady that is at least in part due to biochemical or physiological processes associated with serotonin receptors or transporters. The Background of the Invention (see above) teaches examples of acute or chronic ailments, diseases or maladies that are caused or exacerbated by biochemical or physiological processes associated with serotonin receptors or transporters. One of ordinary skill in the art will be able to accumulate, by reference to the scientific literature, a more comprehensive list of acute or chronic ailments, diseases or maladies that are caused or exacerbated by biochemical or physiological processes associated with serotonin receptors or transporters. The present invention contemplates pharmaceutical formulations of ligands of the present invention that will be of medicinal value against the aforementioned acute or chronic ailments, diseases or maladies.

Biochemical Activity at Cellular Receptors, and Assays to Detect that Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for μ-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes Ca<2+> as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test. compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–> and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986) Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma-subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl. Acad. Sci. 84.:7920–7924); human alpha 2 (Kobilka et al. (1987) Science 238:650–656); hamster beta 2 (Dixon et al. (1986) Nature 321:75–79); and the like); dopamine receptors (e.g., human D2 (Stormann et al. (1990) Molec. Pharm. 37:1–6); rat (Bunzow et al. (1988) Nature 336:783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included it must be a regulatable promoter, At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surf protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Pharmaceutical Compositions/Formulations

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue, hard gelatin capsules, soft gelatin capsules, mouth sprays, emulsions, microemulsions; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 per cent to about 99.9 percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, e.g., sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, sodium stearate, zinc stearate, magnesium stearate, solid polyethylene glycols, sodium lauryl sulfate, and mixtures thereof; (10) coloring agents; and (11) controlled release agents, such as ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intrarectally, for example, as a pessary, cream or foam; (5) sublingually; (6) ocularly; (7) transdermally; (8) nasally; or (9) buccally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and C O., San Francisco, U.S.A., 1969 or "Livestock Feeds and Feeding" O and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-Oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-Sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of 1-[1-(4-chloro-phenyl)-cyclobutanecarbonyl]-piperidin-3-ylmethyl alcohol
(1)

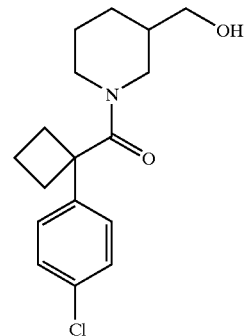

To a solution of 3-piperidinemethanol (5.0 g, 43.4 mmol), 1-(4-chlorophenyl)-1-cyclobutanecarboxylic acid (9.14 g, 43.4 mmol), and diisopropylethylamine (11.22 g, 86.8 mmol) in dichloromethane (100 mL) at 0° C. was added PyBroP® (22.26 g, 47.8 mmol). The reaction was stirred at 0° C. for 1 h and then at room temperature for 4 h. The reaction mixture was washed successively with water, 1 N HCl, water, sat. sodium bicarbonate solution, and water (100 mL each). The organic layer was dried over anhydrous sodium sulfate, filtered and concentrated by rotary evaporation. The residue was purified by chromatography on silica gel, eluting with dichloromethane/methanol (96:4) to give 5.8 g of the amide 1 as a thick gum.

Example 2

Synthesis of Methanesulfonic acid 1-[1-(4-chloro-phenyl)-cyclobutanecarbonyl]-piperidin-3-ylmethyl ester (2)

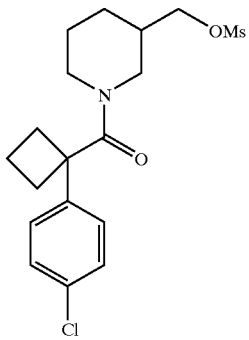

The amide derivative 1 (5.0 g, 16.3 mmol) was dissolved in dichloromethane (50 mL) and cooled to 0° C. To this solution was added triethylamine (5.0 mL) followed by dropwise addition of methanesulfonyl chloride (2.05 g, 17.9 mmol). The reaction was stirred at 0° C. for 1 h, and then at room temperature overnight. The reaction mixture was washed successively with water, 1 N HCl, water, sat. sodium bicarbonate solution, and water (100 mL each). The organic layer was dried over anhydrous sodium sulfate, filtered and concentrated by rotary evaporation. The residue was purified by chromatography on silica gel, eluting with hexane/ethyl acetate (2:1) to give 2 (4.45 g, 71%) as a tan gum; $C_{18}H_{24}ClNO_4S$, LRMS (m/z)=386 (MH+).

Example 3

Synthesis of [1-(4-Chloro-phenyl)-cyclobutyl]-{3-[4-(2-methoxy-phenyl)-piperazin-1-ylmethyl]-piperidin-1-yl}-methanone (3)

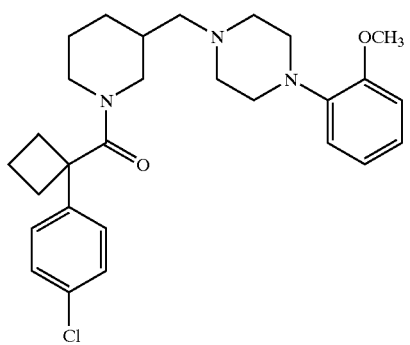

To a solution of 2 (1.0 g, 2.60 mmol) in acetonitrile (25 mL) was added 1-(2-methoxyphenyl)piperazine (0.55 g, 2.86 mmol) and triethylamine (2 mL). The reaction was stirred and refluxed for 20 h. After cooling to room temperature, most of solvent was removed by rotary evaporation. The reaction mixture was partitioned between dichloromethane and water (50 mL each), and the organic layer was washed with sat. sodium carbonate (50 mL) and water. The organic layer was dried over anhydrous sodium sulfate, filtered and concentrated by rotary evaporation. The organic residue was purified by flash chromatography on silica gel, eluting with dichloromethane/2.0 M ammonia in ethyl alcohol (96:4) to give 3 (0.54 g, 43%) as a light brown solid; $C_{28}H_{36}ClN_3O_2$, LRMS (m/z)=483 (MH+).

Example 4

Synthesis of (3-{4-[Bis-(4-fluoro-phenyl)-methyl]-piperazin-1-ylmethyl}-piperidin-1-yl)-[1-(4-chloro-phenyl)-cyclobutyl]-methanone (4)

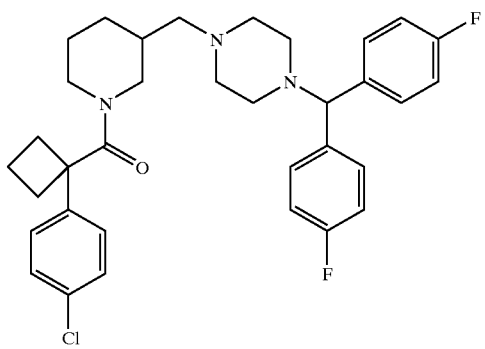

Compound 4 was prepared using the method described in Example 3, starting with 1-bis(4-fluorophenyl)methyl piperazine (0.82 g, 2.86 mmol) to give 4 (0.69 g, 46%); $C_{34}H_{38}ClF_2N_3O$, LRMS (m/z)=579 (MH+).

Example 5

Synthesis of [1-(4-Chloro-phenyl)-cyclobutyl]-{3-[4-(3-chloro-phenyl)-piperazin-1-ylmethyl]-piperidin-1-yl}-methanone (5)

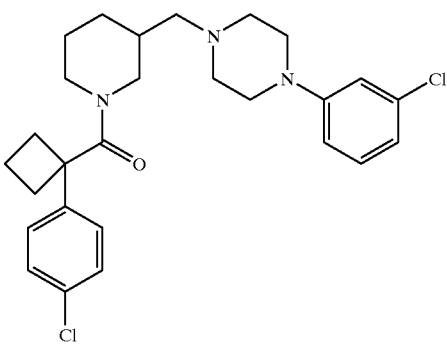

Compound 5 was prepared using the method described in Example 3, starting with 1-(3-chloropheyl)piperazine (0.56 g, 2.86 mmol) to give 5 (0.49 g, 39%); $C_{27}H_{33}Cl_2N_3O$, LRMS (m/z)=487 (MH+).

Example 6

Synthesis of [1-(4-Chloro-phenyl)-cyclobutyl]-{3-[4-(4-fluoro-phenyl)-piperazin-1-ylmethyl]-piperidin-1-yl}-methanone (6)

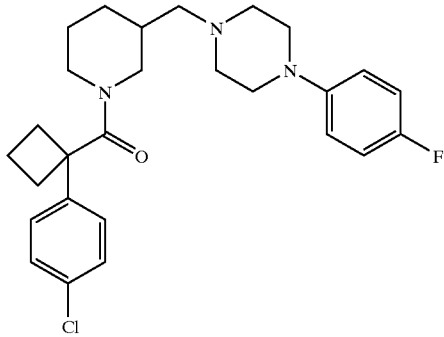

Compound 6 was prepared using the method described in Example 3, starting with 1-(4-fluorophenyl)piperazine (0.51 g, 2.86 mmol) to give 6 (0.60 g, 49%); $C_{27}H_{33}ClFN_3O$, LRMS (m/z)=471 (MH+).

Example 7

[1-(4-Chloro-phenyl)-cyclobutyl]-{3-[4-(2-chloro-phenyl)-piperazin-1-ylmethyl]-piperidin-1-yl}-methanone (7)

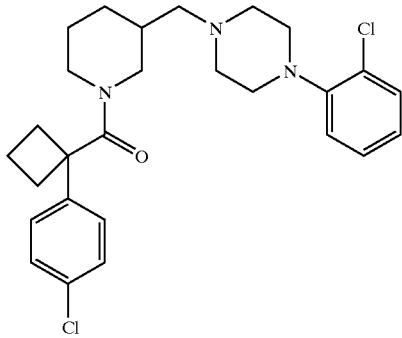

Compound 7 was prepared using the method of described in Example 3, starting with compound 2 (1.0 g, 2.60 mmol), 1-(2-chlorophenyl)piperazine (0.56 g, 2.86 mmol), and cesium carbonate (1.27 g, 3.90 mmol) to give 7 (0.53 g, 42%); $C_{27}H_{33}Cl_2N_3O$, LRMS (m/z)=487 (MH+).

Example 8

[1-(4-Chloro-phenyl)-cyclobutyl]-{3-[4-(2-fluoro-phenyl)-piperazin-1-ylmethyl]-piperidin-1-yl}-methanone (8)

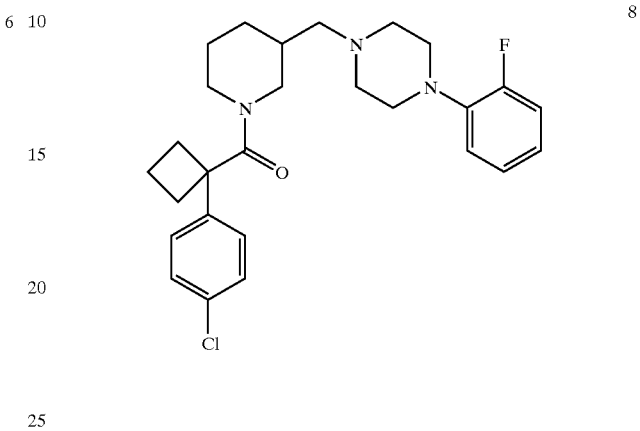

Compound 8 was prepared using the method described in Example 3, starting with compound 2 (1.0 g, 2.60 mmol), 1-(2-fluorophenyl)piperazine (0.51 g, 2.86 mmol), and cesium carbonate (1.27 g, 3.90 mmol) to give 8 (0.56 g, 46%); $C_{27}H_{33}ClFN_3O$, LRMS (m/z)=471 (MH+).

Example 9

[1-(4-Chloro-phenyl)-cyclobutyl]-{3-[4-(2-trifluoromethoxy-phenyl)-piperazin-1-ylmethyl]-piperidin-1-yl}-methanone (9)

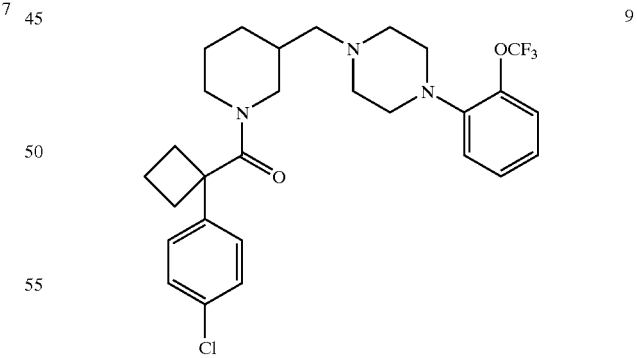

Compound 9 was prepared using the method described in Example 3, starting with compound 2 (1.0 g, 2.60 mmol), 1-(2-trifluoromethoxyphenyl)piperazine (0.70 g, 2.86 mmol), and cesium carbonate (1.27 g, 3.90 mmol) to give 9 (0.45 g, 32%); $C_{28}H_{33}ClF_3N_3O_2$, LRMS (m/z)=537 (MH+).

Example 10

[1-(4-Chloro-phenyl)-cyclobutyl]-{3-[4-(2-isopropoxy-phenyl)-piperazin-1-ylmethyl]-piperidin-1-yl}-methanone (11)

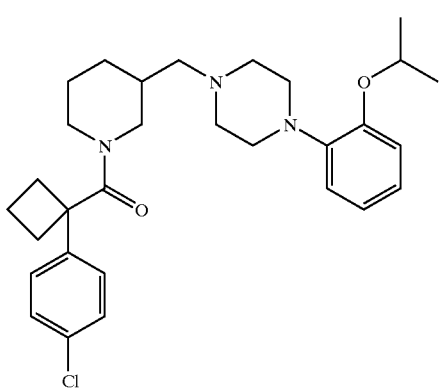

Compound 11 was prepared using the method described in Example 3, starting with compound 2 (1.0 g, 2.60 mmol), 1-(2-isopropoxyphenyl)piperazine (0.63 g, 2.86 mmol), and cesium carbonate (1.27 g, 3.90 mmol) to give 11 (0.49 g, 37%); $C_{30}H_{40}ClN_3O_2$, LRMS (m/z)=511 (MH+).

Example 11

[1-(4-Chloro-phenyl)-cyclobutyl]-{3-[4-(2-hydroxy-phenyl)-piperazin-1-ylmethyl]-piperidin-1-yl}-methanone (12)

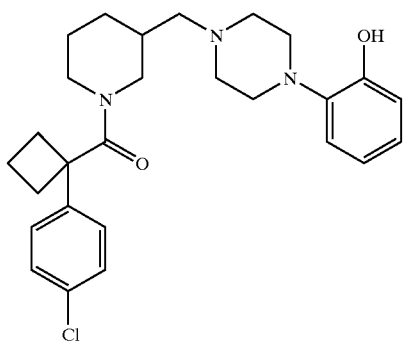

Compound 12 was prepared using the method described in Example 3, starting with compound 2 (1.0 g, 2.60 mmol), 1-(2-hydroxyphenyl)piperazine (0.51 g, 2.86 mmol), and cesium carbonate (1.27 g, 3.90 mmol) to give 12 (0.39 g, 32%); $C_{27}H_{34}ClN_3O_2$, LRMS (m/z)=469 (MH+).

Example 12

Synthesis of 3-Hydroxymethyl-piperidine-1-carboxylic acid tert-butyl ester

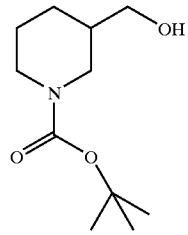

A 500 mL round bottom flask was charged with potassium carbonate (17 g, 0.123 mol), piperdin-3-yl methanol (4.72 g, 0.041 mol), and a 1:1 mixture of THF/water (200 mL). Solid di tert-butyl dicarbonate (8.94 g, 0.041 mol) was added to the stirring reaction mixture. After completion of addition the reaction mixture was stirred at room temperature for 12 h. The aqueous layer was separated from the reaction mixture and extracted with ethyl acetate (3×100 mL). The combined organic layers were dried over sodium sulfate and concentrated to yield the desired product (9.41 g).

Example 13

Synthesis of 3-Methanesulfonyloxymethyl-piperidine-1-carboxylic acid tert-butyl ester

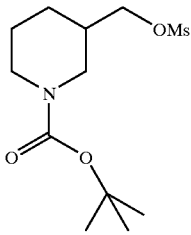

To a solution of 3-hydroxymethyl-piperidine-1-carboxylic acid tert-butyl ester (9.41 g, 0.048 mol) in dichloromethane (200 mL) at room temperature was added iPr$_2$NEt (14.1 g, 0.110 mol), followed by MsCl (5.5 g, 0.048 mol). The reaction mixture was allowed to stir for one hour before concentrating and purifying the resulting residue by silica gel chromatography (1:1 hexane:ethyl acetate). The desired compound was obtained as an oil (11.06 g, 86%).

Example 14

Synthesis of 3-[4-(2-Methoxy-phenyl)-piperazin-1-ylmethyl]-piperidine-1-carboxylic acid tert-butyl ester

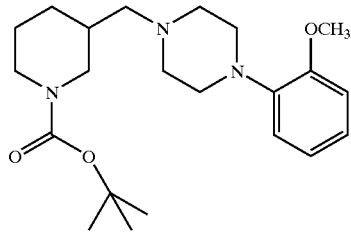

To a solution of 3-methanesulfonyloxymethyl-piperidine-1-carboxylic acid tert-butyl ester (11.06 g, 0.04 mol) in acetonitrile (180 mL) was added potassium carbonate (26 g, 0.19 mol) followed by 1-(2-methoxy-phenyl) piperazine (7.25 g, 0.04 mol). After completion of addition the reaction mixture was heated to reflux. After 12 h the reaction mixture was cooled down to room temperature and quenched with water. The aqueous layer was extracted with ethyl acetate (3×100 mL). The combined organic layers were dried over sodium sulfate and concentrated to yield an oil. This crude material was purified using silica gel chromatography (7:3:0.05 Hexane:EtOAc:2M $NH_3$ in EtOH) to afford the desired compound in good yield (8.0 g, 55%). $C_{22}H_{35}N_3O_3$, LRMS (m/z)=390 (MH+).

Example 15

Synthesis of 3-[4-(2-Methoxy-phenyl)-piperazin-1-ylmethyl]-piperidine-1-carboxylic acid tert-butyl ester

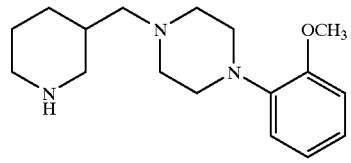

3-[4-(2-Methoxy-phenyl)-piperazin-1-ylmethyl]-piperidine-1-carboxylic acid tert-butyl ester (8.0 g, 0.021 mol) was dissolved in dichloromethane (51 mL) and cooled to 0° C. in an ice bath. Concentrated trifluoroacetic acid (51 mL) was added dropwise to the cooled reaction mixture. After completion of addition the reaction mixture continued stirring at 0° C. After one hour the reaction mixture was concentrated to yield the TFA salt of the desired product (6.0 g). $C_{17}H_{27}N_3O$, LRMS (m/z)=290 (MH+).

Example 16

Synthesis of 1-{1-[4-Chloro-phenyl)-cyclobutylmethyl]-piperidin-3-ylmethyl}-4-(2-methoxy-phenyl)-piperazine

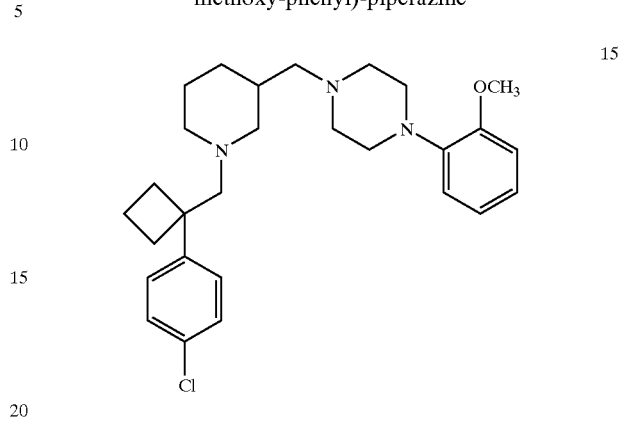

A solution of 3 (94 mg, 0.195 mmol) in toluene (1.0 mL) was cooled to 0° C. RedAl (138 mg, 0.65 mmol) was added dropwise to the stirring reaction mixture. After completion of addition the reaction mixture continued stirring at room temperature. After 12 h the reaction mixture was quenched with water. The aqueous layer was extracted with ethyl acetate (3×5 mL). The combined organic layers were dried over sodium sulfate and concentrated to yield a crude oil The crude material was purified using silica gel chromatography (1:1:0.5% hexane:EtOAc:2M $NH_3$ in EtOH) to afford 15 (7.0 mg, 76%). $C_{28}H_{38}ClN_3O$, LRMS (m/z)=468 (MH+).

Example 17

Synthesis of [1-[4-Chloro-phenyl)-cyclopropyl]-{3-[4-(2-methoxy-phenyl)-piperazin-1-ylmethyl]-piperidin-1-yl}-methanone

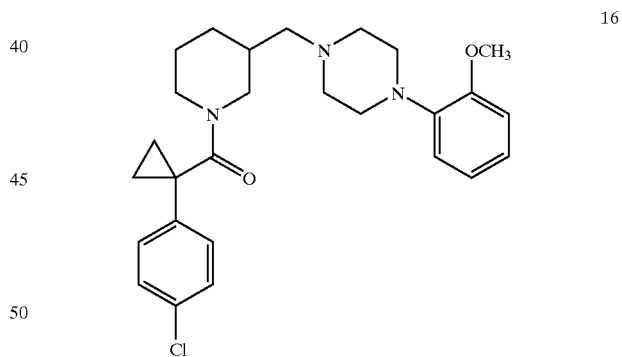

A solution of 3-[4-(2-methoxy-phenyl)-piperazin-1-ylmethyl]-piperidine-1-carboxylic acid tert-butyl ester (1.0 g, 2.49 mmol), 1-(4-chloro-phenyl)-cyclopropylcarboxylic acid (0.731 g, 3.72 mmol), diisopropylethyl amine (1.6 g, 12.39 mmol) in dichloromethane (12 mL) was stirred at room temperature. PyBroP (1.72 g, 3.72 mmol) was added and the reaction mixture continued stirring at room temperature. After 12 h the reaction mixture was quenched with 10% KOH. The aqueous layer was extracted with ethyl acetate. The combined organic layers were dried over sodium sulfate and concentrated to yield a crude oil. The crude material was purified using silica gel chromatography (55:40:5 hexane:ethyl acetate:2M $NH_3$ in EtOH) to yield 16 (40 mg). $C_{27}H_{34}ClN_3O_2$, LRMS (m/z)=468 (MH+).

Example 18

Synthesis of [1-(4-Chloro-phenyl)-cyclopentyl]-(3-hydroxymethyl-piperidin-1-yl)-methanone

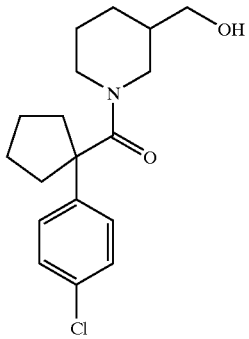

A solution of piperdin-3-yl methanol (0.342 g, 2.97 mmol), 1-(4-chloro-phenyl)-cyclopentylcarboxylic acid (1.0 g, 4.45 mmol), diisopropylethyl amine (1.9, 15.00 mmol) in dichloromethane (7 mL) was stirred at room temperature. PyBroP (2.07 g, 4.45 mmol) was added and the reaction mixture continued stirring at room temperature. After 12 h the reaction mixture was quenched with 10% KOH. The aqueous layer was extracted with ethyl acetate. The combined organic layers were dried over sodium sulfate and concentrated to yield a crude oil. The crude material was purified using silica gel chromatography (95:5 hexane:ethyl acetate) to yield the desired compound (1.50 g). $C_{18}H_{24}ClNO_2$, LRMS (m/z)=322 (MH+).

Example 19

Synthesis of Methanesulfonic acid 1-[1-(4-Chloro-phenyl)-cyclopentanecarbonyl]-piperidin-3-ylmethyl ester

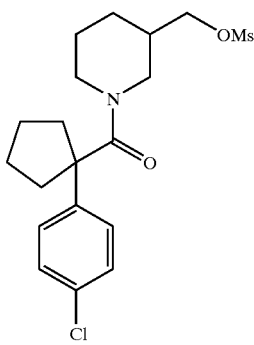

To a solution of [1-(4-chloro-phenyl)-cyclopentyl]-(3-hydroxymethyl-piperidin-1-yl)-methanone (0.5 g, 1.55 mmol) in dichloromethane (9.5 mL) at room temperature was added iPr$_2$NEt (0.5 g, 3.9 mmol) followed by MsCl (0.214 g, 1.86 mmol). The reaction mixture was allowed to stir for one hour before concentrating and purifying the resulting residue by silica gel chromatography (gradient 2.5–100% EtOAc in hexane). The desired compound was obtained as an oil (0.345 g, 56%). $^{13}$C (100 MHz, CDCl$_3$, partial) δ 174.0, 144.0, 131.8, 128.8, 126.5, 70.8, 58.1, 35.3, 26.5, 24.9. $^1$H (300 MHz, CDCl$_3$) δ 7.26–7.24 (m, 2H), 7.13–7.10 (m, 2H), 4.61–1.86 (m, 19H), 1.67 (s, 3H).

Example 20

Synthesis of 1-[4-Chloro-phenyl)-cyclopentyl]-{3-[4-(2-methoxy-phenyl)-piperazin-1-ylmethyl]-piperidin-1-yl}-methanone

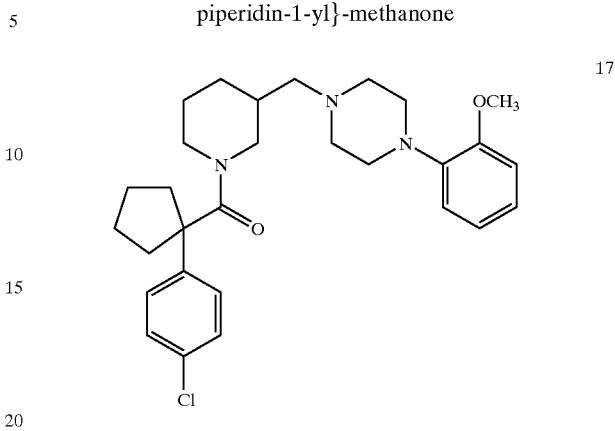

To a solution of methanesulfonic acid 1-[1-(4-chloro-phenyl)-cyclopentanecarbonyl]-piperidin-3-ylmethyl ester (0.145 g, 0.36 mmol) in acetonitrile (4.0 mL) at room temperature was added 1-(2-methoxy-phenyl)-piperazine (0.077 g, 0.36 mmol) followed by triethylamine (0.30 mL). The reaction mixture was refluxed overnight. After cooling down to room temperature the reaction mixture was diluted with water and extracted with dichloromethane (3×10 mL). The combined organic layers were dried over sodium sulfate and concentrated to yield a crude oil. The resulting residue was purified by silica gel chromatography (4:1 ethyl acetate:DCM) to afford 17 as an oil (80.3 mg, 34%). $C_{29}H_{38}ClN_3O_2$, LRMS (m/z)=497 (MH+).

Example 21

Synthesis of 1-[1-(4-Chloro-phenyl)-cyclopropanecarbonyl]-piperidine-3-carboxylic acid ethyl ester

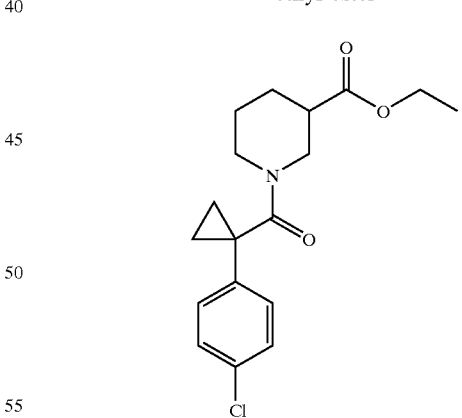

A solution of piperidine-3-carboxylic acid ethyl ester (10.0 g, 0.032 mol), 1-(4chloro-phenyl)-cyclopropylcarboxylic acid (9.57 g, 0.049 mol), diisopropylethyl amine (21.0 g, 0.16 mol) in dichloromethane (160 mL) was stirred at room temperature. PyBroP (22.6 g, 0.49 mol) was added and the reaction mixture continued stirring at room temperature. After 12 h the reaction mixture was quenched with 10% KOH. The aqueous layer was extracted with ethyl acetate. The combined organic layers were dried over sodium sulfate and concentrated to yield a crude oil.

The crude material was purified using silica gel chromatography (80:20 hexane:ethyl acetate) to yield the amide (18.0 g).

Example 22

Synthesis of {1-[1-(4-Chloro-phenyl)-cyclomethyl]-pipidin-3-yl)-methanol

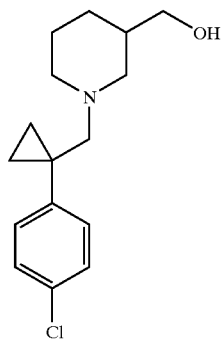

To a cooled (0° C.) solution of 1-[1-(4-chloro-phenyl)-cyclopropanecarbonyl]-piperidine-3-carboxylic acid ethyl ester (18.24 g, 0.054 mol) in THF (270 mL) was added lithium aluminum hydride (1.0 M in THF, 270 mL). After completion of addition the reaction proceeded at room temperature. After 4 hours the reaction mixture was quenched with 10% HCl (aq.). The aqueous layer was separated and basified with 10% NaOH (aq.). The neutral aqueous layer was extracted with ethyl acetate (3×200 mL). The combined organic layers were dried over sodium sulfate and concentrated to yield a crude oil. The crude material was purified using silica gel chromatography (100% EtOAc) to afford the desired compound in good yield (8.34 g). $C_{16}H_{22}ClNO$, LRMS (m/z)=280 (MH+).

Example 23

Synthesis of Methanesulfonic acid 1-[1-(4-chloro-phenyl)-cyclopropylmethyl]-piperidin-3-ylmethyl ester

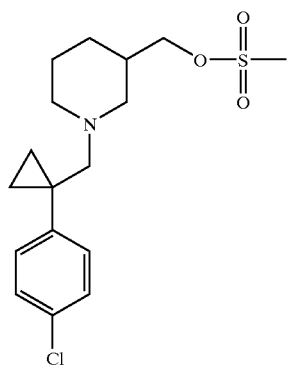

To a solution of {1-[1-(4-chloro-phenyl)-cyclomethyl]-pipidin-3-yl)-methanol (2.62 g, 0.009 mol) in dichloromethane (40 mL) at room temperature was added iPr$_2$NEt (3.92 mL) followed by MsCl (0.79 mL, 0.010 mol). The reaction mixture was allowed to stir for one hour before concentrating and purifying the resulting residue by silica gel chromatography (90:10 DCM:2M NH$_3$ in EtOH). The desired compound was obtained as an oil (2.94 g). $^{13}$C NMR (100 MHz, CDCl$_3$) δ 143.6, 131.5, 130.3, 128.2, 72.7, 67.5, 56.4, 54.3, 37.1, 35.6, 26.6, 23.9, 22.8, 13.2, 13.1.

Example 24

Synthesis of 1-{1-[1-(4-Choro-phenyl)-cyclopropylmethyl]-piperidin-3ylmethyl}-4-(2-methoxy-phenyl)-piperazine

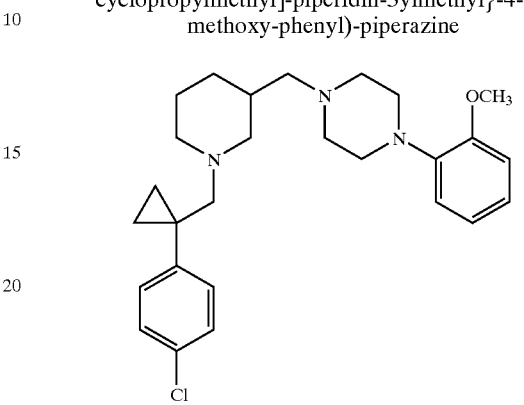

To a solution of methanesulfonic acid 1-[1-(4-chloro-phenyl)-cyclopropylmethyl]-piperidin-3-ylmethyl ester (2.94 g, 8.20 mmol) in acetonitrile (40.0 mL) at room temperature was added 1-(2-methoxy-phenyl)-piperazine (1.58 g, 8.20 mmol) followed by potassium carbonate (13.35 g, 41.0 mmol). The reaction mixture was refluxed overnight. After cooling down to room temperature the reaction mixture was diluted with water and extracted with EtOAc (3×50 mL). The combined organic layers were dried over sodium sulfate and concentrated to yield a crude oil. The resulting residue was purified by silica gel chromatography (96:4 DCM: 2M NH$_3$ in EtOH) to obtain the desired compound as an oil (2.04 g). $^{13}$C NMR (100 MHz, CDCl$_3$) δ 152.5, 143.9, 141.8, 131.5, 130.4, 128.2, 123.1, 121.3, 118.4, 111.5, 67.8, 63.0, 59.5, 55.6, 55.2, 54.2, 51.0, 33.5, 29.8, 25.2, 23.1, 13.4, 13.1.

Example 25

Assay for Binding to Human Dopamine $D_{2L}$ ($D_{2A}$) Receptors

This assay measures binding of [$^3$H]Spiperone (IC50=2.8 nM; Ki=0.93 nM) to human dopamine $D_{2L}$ ($D_{2A}$) receptors. CHO cells stably transfected with a plasmid encoding the human dopamine $D_{2L}$ receptor were used to prepare membranes in modified Tris-HCl pH 7.4 buffer using standard techniques. A 20 μg aliquot of membrane was incubated with 0.16 nM [$^3$H]Spiperone for 120 minutes at 25° C. Non-specific binding was estimated in the presence of 10 μM haloperidol. Membranes were filtered and washed 3 times and the filters were counted to determine [$^3$H]Spiperone specifically bound. Compounds of the present invention were screened at 10 and 1 μM. See Bunzow, J. R. et al. "Cloning and expression of rat $D_2$ dopamine receptor cDNA" Nature 336: 783–787, 1988; Grandy, D. K. et al. "Cloning of the cDNA and gene for a human $D_2$ dopamine receptor" Proc. Natl. Acad. Sci. U.S.A. 86: 9762–9766, 1989; and Hayes, G. et al. "Structural subtypes of the dopamine $D_2$ receptor are functionally distinct: Expression of the clone $D_{2A}$ and $D_{2B}$ subtypes in a heterologous cell line" Mol. Endocrin. 6: 920–926, 1992.

Example 26
Assay for Binding to Human Dopamine $D_{2S}$ ($D_{2B}$) Receptors This assay measures binding of [$^3$H]Spiperone (IC50=0.58 nM; Ki=0.21 nM) to human dopamine $D_{2S}$ ($D_{2B}$) receptors. CHO cells stably transfected with a plasmid encoding the human dopamine $D_{2S}$ receptor were used to prepare membranes in modified Tris-HCl pH 7.4 buffer using standard techniques. A 15 µg aliquot of membrane was incubated with 0.16 nM [$^3$H]Spiperone for 120 minutes at 25° C. Non-specific binding was estimated in the presence of 10 µM haloperidol. Membranes were filtered and washed 3 times and the filters were counted to determine [$^3$H]Spiperone specifically bound. Compounds of the present invention were screened at 10 and 1 µM. See Bunzow, J. R. et al. "Cloning and expression of rat $D_2$ dopamine receptor cDNA" Nature 336: 783–787, 1988; Grandy, D. K. et al. "Cloning of the cDNA and gene for a human $D_2$ dopamine receptor" Proc. Natl. Acad. Sci. U.S.A. 86: 9762–9766, 1989; and Hayes, G. et al. "Structural subtypes of the dopamine $D_2$ receptor are functionally distinct: Expression of the clone $D_{2A}$ and $D_{2B}$ subtypes in a heterologous cell line" Mol. Endocrin. 6: 920–926, 1992.

Example 27
Assay for Binding to Human Dopamine $D_3$ Receptors

This assay measures binding of [$^3$H]Spiperone (IC50=2.9 nM; Ki=0.99 nM) to human dopamine $D_3$ receptors. CHO cells stably transfected with a plasmid encoding the human dopamine $D_3$ receptor were used to prepare membranes in modified Tris-HCl pH 7.4 buffer using standard techniques. A 10 µg aliquot of membrane was incubated with 0.7 nM [$^3$H]Spiperone for 120 minutes at 37° C. Non-specific binding was estimated in the presence of 25 µM S-(−)-sulpiride. Membranes were filtered and washed 3 times and the filters were counted to determine [$^3$H]Spiperone specifically bound. Compounds of the present invention were screened at 10 and 1 µM. See Sokoloff, P. et al. "Molecular cloning and characterization of a novel dopamine receptor ($D_3$) as a target for neuroleptics" Nature 347: 146–151, 1990.

Example 28
Assay for Binding to Human Dopamine $D_{4.4}$ Receptors

This assay measures binding of [$^3$H]Spiperone (IC50=0.8 nM; Ki=0.3 nM) to human dopamine $D_{4.4}$ receptors. CHO cells stably transfected with a plasmid encoding the human dopamine $D_{4.4}$ receptor were used to prepare membranes in modified Tris-HCl pH 7.4 buffer using standard techniques. A 100 µg aliquot of membrane was incubated with 1.2 nM [$^3$H]Spiperone for 120 minutes at 25° C. Non-specific binding was estimated in the presence of 10 µM haloperidol. Membranes were filtered and washed 3 times and the filters were counted to determine [$^3$H]Spiperone specifically bound. Compounds of the present invention were screened at 10 and 1 µM. See Van Tol, H. H. M. et al. "Cloning of the gene for a human dopamine $D_4$ receptor with high affinity for the antipsychotic clozapine" Nature 350: 610–614, 1991.

Example 29
Assay for Binding to Rat 5-HT$_1$ Receptors

This assay measures binding of [$^3$H]5-Hydroxytryptamine (5-HT) (IC50=8.3 nM; Ki=3.6 nM) non-selectively to 5-HT$_1$ receptors. Cerebral cortical membranes of male Wistar derived rats weighing 175±25 g were prepared in Tris-HCl pH 7.6 buffer using standard techniques. A 10 mg aliquot of membrane was incubated with 2 nM [$^3$H]5-HT for 10 minutes at 37° C. Non-specific binding was estimated in the presence of 10 µM 5-HT. Membranes were filtered and washed 3 times and the filters were counted to determine [$^3$H]5-HT specifically bound. Compounds of the present invention were screened at 10 and 1 µM. See Middlemiss, D. N. "Stereoselective blockade at [$^3$H]5-HT binding sites and at the 5-HT autoreceptor by propranolol" Eur. J. Pharmacol. 101: 289–293, 1984.

Example 30
Assay for Binding to Human 5-HT$_{1A}$ Receptors

This assay measures binding of [$^3$H]8-OH-DPAT (IC50=8.3 nM; Ki=3.6 nM) to human serotonin 5-HT$_{1A}$ receptors. CHO cells stably transfected with a plasmid encoding the human serotonin 5-HT$_{1A}$ receptor were used to prepare membranes in modified Tris-HCl pH 7.4 buffer using standard techniques. An 8 µg aliquot of membrane was incubated with 1.5 nM [$^3$H]8-OH-DPAT for 60 minutes at 25° C. Non-specific binding was estimated in the presence of 10 µM metergoline (IC50=16 nM; Ki=9.0 nM). Membranes were filtered and washed 3 times and the filters were counted to determine [$^3$H]8-OH-DPAT specifically bound. Compounds of the present invention were screened at 10 and 1 µM. See Martin, G. R. and Humphrey, P. P. A. "Receptor for 5-hydroxytryptamine: current perspectives on classification and nomenclature" Neuropharmacol. 33: 261–273, 1994.

Example 31
Assay for Binding to Rat 5-HT$_2$ Receptors

This assay measures binding of [$^3$H]Ketanserin (IC50=2.1 nM; Ki=13 nM) to serotonin 5-HT$_2$ receptors. Whole brain (except cerebellum) membranes of male Wistar derived rats weighing 175±25 g were prepared in Tris-HCl pH 7.7 buffer using standard techniques. A 10 mg aliquot of membrane was incubated with 0.5 nM [$^3$H]Ketanserin for 40 minutes at 25° C. Non-specific binding was estimated in the presence of 1 µM ketanserin. Membranes were filtered and washed 3 times and the filters were counted to determine [$^3$H]Ketanserin specifically bound. Compounds of the present invention were screened at 10 and 1 µM. See Leysen, J. E. et al. "[$^3$H]Ketanserin (R 41 468), a selective [$^3$H]ligand for serotonin$_2$ receptor binding sites" Mol. Pharmacol. 21: 301–314, 1982.

Example 32
Assay for Binding to Human 5-HT$_{2A}$ Receptors

This assay measures binding of [$^3$H]Ketanserin (IC50=0.65 nM; Ki=0.19 nM) to human serotonin 5-HT$_{2A}$ receptors. CHO-K1 cells stably transfected with a plasmid encoding the human serotonin 5-HT$_{2A}$ receptor were used to prepare membranes in modified Tris-HCl pH 7.7 buffer using standard techniques. A 30 µg aliquot of membrane protein was incubated with 0.5 nM [$^3$H]Ketanserin for 60 minutes at 25° C. Non-specific binding was estimated in the presence of 1 µM mianserin. Membranes were filtered and washed 3 times and the filters were counted to determine [$^3$H]Ketanserin specifically bound. Compounds of the present invention were screened at 10 and 1 µM. See Bonhaus, D. W. et al. "The pharmacology and distribution of human 5-hydroxytryptamine$_{2B}$ (5-HT$_{2B}$) receptor gene products: comparison with 5-HT$_{2A}$ and 5-HT$_{2C}$ receptors" Brit. J. Pharmacol. 115: 622–628, 1995; and Saucier, C and Albert, P. R. "Identification of an endogenous 5-hydroxytryptamine$_{2A}$ receptor in NIH-3T3 cells: agonist-induced down-regulation involves decreases in receptor RNA and number" J. Neurochem. 68: 1998–2011, 1997.

Example 33
Assay for Binding to Human 5-HT$_{2B}$ Receptors

This assay measures binding of [$^3$H]LSD to human serotonin 5-HT$_{2B}$ receptors. CHO-K1 cells stably transfected with a plasmid encoding the human serotonin 5-HT$_{2B}$ receptors were used to prepare membranes in modified Tris-HCl pH 7.4 buffer using standard techniques. A 30 µg aliquot of membrane protein was incubated with 1.2 nM [$^3$H]LSD for 60 minutes at 37° C. Non-specific binding was estimated in the presence of 10 µM serotonin. Membranes were filtered and washed 3 times and the filters were counted to determine [$^3$H]LSD specifically bound. Compounds of the present invention were screened at 10 and 1 µM. See Bonhaus, D. W. et al. "The pharmacology and distribution of human 5-hydroxytryptamine$_{2B}$ (5-HT$_{2B}$) receptor gene products: comparison with 5-HT$_{2A}$ and 5-HT$_{2C}$ receptors" Brit. J. Pharmacol. 115: 622–628, 1995.

Example 34
Assay for Binding to Human 5-HT$_{2C}$ Receptors

This assay measures binding of [$^3$H]Mesulergine (IC50=0.74 nM; Ki=0.39 nM) to human serotonin 5-HT$_{2C}$ receptors. CHO-K1 cells stably transfected with a plasmid encoding the human serotonin 5-HT$_{2C}$ receptor were used to prepare membranes in modified Tris-HCl pH 7.7 buffer using standard techniques. A 3.2 µg aliquot of membrane protein was incubated with 1.0 nM [$^3$H]Mesulergine for 60 minutes at 25° C. Non-specific binding was estimated in the presence of 1 µM mianserin. Membranes were filtered and washed 3 times and the filters were counted to determine [$^3$H]Mesulergine specifically bound. Compounds of the present invention were screened at 10 and 1 µM. See Wolf, W. A. and Schutz, J. S. "The serotonin 5-HT$_{2C}$ receptor is a prominent serotonin receptor in basal ganglia: evidence from functional studies on serotonin-mediated phosphoinositide hydrolysis" J. Neurochem. 69: 1449–1458, 1997.

Example 35
Assay for Binding to Human 5-HT$_6$ Receptors

This assay measures binding of [$^3$H]LSD (lysergic acid diethylamide) to human serotonin 5-HT$_6$ receptors. HeLa/E6-7 cells stably transfected with a plasmid encoding the human serotonin 5-HT$_6$ receptor were used to prepare membranes in modified Tris-HCl pH 7.4 buffer using standard techniques. A 30 µg aliquot of membrane was incubated with 1.5 nM [$^3$H]LSD for 120 minutes at 37° C. Non-specific binding was estimated in the presence of 5 µM 5-HT. Membranes were filtered and washed 3 times and the filters were counted to determine [$^3$H]LSD specifically bound. Compounds of the present invention were screened at 10 and 1 µM. See Monsma, Jr., F. J. et al. "Cloning and expression of a novel serotonin receptor with high affinity for tricyclic psychotropic drugs" Mol. Pharmacol. 43: 320–327, 1993.

Example 36
Assay for Binding to Human 5-HT$_7$ Receptors

This assay measures binding of [$^3$H]LSD (lysergic acid diethylamide) to human serotonin 5-HT$_7$ receptors. CHO cells stably transfected with a plasmid encoding the human serotonin 5-HT$_7$ receptor were used to prepare membranes in modified Tris-HCl pH 7.4 buffer using standard techniques. A 50 µg aliquot of membrane was incubated with 5.5 nM [$^3$H]LSD for 120 minutes at 25° C. Non-specific binding was estimated in the presence of 10 µM serotonin. Membranes were filtered and washed 3 times and the filters were counted to determine [$^3$H]LSD specifically bound. Compounds of the present invention were screened at 10 and 1 µM. See Roth, B. L. et al. "Binding of typical and atypical antipschotic agents to 5-hydroxytryptamine-6 and 5-hydroxytryptamine-7 receptors" J. Pharmacol. Exp. Ther. 268: 1403–1410, 1994; and Shen, Y. et al. "Molecular cloning and expression of a 5-hydroxytryptamine 7 serotonin receptor subtype" J. Biol. Chem. 268: 18200–18204, 1993.

Example 37
Assay for Binding to Rat Adrenergic $\alpha_{1A}$ Receptors

This assay measures binding of [$^3$H]Prazosin (IC50=0.16 nM; Ki=0.065 nM) to adrenergic $\alpha_{1A}$ receptors. Submaxillary gland membranes of male Wistar derived rats weighing 175±25 g were prepared in modified Tris-HCl pH 7.4 buffer using standard techniques. A 5 mg aliquot of membrane was incubated with 0.25 nM [$^3$H]Prazosin for 60 minutes at 25° C. Non-specific binding was estimated in the presence of 10 µM phentolamine. Membranes were filtered and washed 3 times and the filters were counted to determine [$^3$H]Prazosin specifically bound. Compounds of the present invention were screened at 10 and 1 µM. See Michel, A. D. et al. "Identification of a single $\alpha_{1A}$-adrenoceptor corresponding to the $\alpha_{1A}$ subtype in rat submaxillary gland" Br. J. Pharmacol. 98: 883–889, 1989.

Example 38
Assay for Binding to Human Adrenergic $\alpha_{1D}$ Receptors

This assay measures binding of [$^3$H]prazosin (IC50=0.88 nM; Ki=0.43 nM) to adrenergic $\alpha_{1D}$ receptors. Membranes (obtained from HEK-293 cells) encoding the human adrenergic $\alpha_{1D}$ receptor were used in modified Tris-HCl, pH 7.4 buffer using standard techniques. A 50 µg aliquot of membrane was incubated with 0.6 nM [$^3$H]prazosin for 60 minutes at 25° C. Non-specific binding was estimated in the presence of 10 µM phentolamine. Membranes were filtered and washed 3 times and the filters were counted to determine [$^3$H]prazosin specifically bound. Compounds of the present invention were screened at 10 and 1 µM. See Kenny, B. A. et al. "Characterization of an $\alpha_{1D}$-adrenoceptor mediating the contractile response of rat aorta to noradrenaline" British Journal of Pharmacology. 115: 981–986, 1995.

Example 39
Assay for Binding to Human Adrenergic $\alpha_{2A}$ Receptors

This assay measures binding of [$^3$H]MK-912 to adrenergic $\alpha_{2A}$ receptors. Membranes (BSR-A2AH) encoding the human adrenergic $\alpha_{2A}$ receptor were used in modified Tris-HCl pH 7.4 buffer using standard techniques. A 6 µg aliquot of membrane was incubated with 1 nM [$^3$H]MK-912 for 60 minutes at 25° C. Non-specific binding was estimated in the presence of 10 µM WB4101. Membranes were filtered and washed 4 times and the filters were counted to determine [$^3$H]MK-912 specifically bound. Compounds of the present invention were screened at 10 and 1 µM. See Uhlén, S. et al. "The novel alpha-2 adrenergic radioligand [$^3$H]MK912 is alpha-2C selective among human alpha-2A, alpha-2B and alpha-2C adrenoceptors" J. Pharmacol. Exp. Ther. 271: 1558–1565, 1994.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by A:

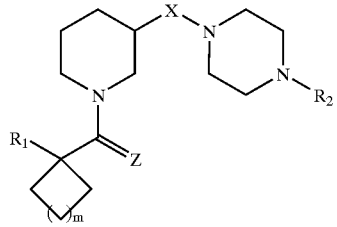

wherein

X represents (C(R)2)n;

Z represents O or H2;

R represents independently for each occurrence H, alkyl, cycloalkyl, aryl, heteroaryl, aralkyl, or heteroaralkyl; or any two geminal instances of R taken together represent O;

R1 represents optionally substituted aryl or heteroaryl; wherein any optional substituent is selected from the group consisting of alkyl, cycloalkyl, fluoro, chloro, bromo, iodo, hydroxy, alkoxy, acyloxy, acyl, nitro, nitroso, amino, acylamino, sulfonyl, and sulfonylamino;

R2 represents optionally substituted aryl, heteroaryl, arylalkyl, heteroarylalkyl, di(aryl)alkyl, or di(heteroaryl)alkyl; wherein any optional substituent is selected from the group consisting of alkyl, cycloalkyl, fluoro, chloro, bromo, iodo, hydroxy, alkoxy, acyloxy, acyl, nitro, nitroso, amino, acylamino, sulfonyl, and sulfonylamino;

m is 0, 1, 2, or 3;

n is 1, 2, or 3; and the stereochemical configuration at any stereocenter of compound represented by A is R, S, or a mixture of these configurations.

2. The compound of claim 1, wherein R represents independently for each occurrence H.

3. The compound of claim 1, wherein R1 represents optionally substituted phenyl.

4. The compound of claim 1, wherein R1 represents 4-chlorophenyl.

5. The compound of claim 1, wherein R2 represents optionally substituted phenyl or diphenylmethyl.

6. The compound of claim 1, wherein R2 represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl.

7. The compound of claim 1, wherein m is 0, 1, or 2.

8. The compound of claim 1, wherein n is 1.

9. The compound of claim 1, wherein R represents independently for each occurrence H; and R1 represents optionally substituted phenyl.

10. The compound of claim 1, wherein R represents independently for each occurrence H; and R1 represents 4-chlorophenyl.

11. The compound of claim 1, wherein R represents independently for each occurrence H; and R2 represents optionally substituted phenyl or diphenylmethyl.

12. The compound of claim 1, wherein R represents independently for each occurrence H; and R2 represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl.

13. The compound of claim 1, wherein R represents independently for each occurrence H; R1 represents optionally substituted phenyl; and R2 represents optionally substituted phenyl or diphenylmethyl.

14. The compound of claim 1, wherein R represents independently for each occurrence H; R1 represents 4-chlorophenyl; and R2 represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl.

15. The compound of claim 1, wherein R represents independently for each occurrence H; R1 represents optionally substituted phenyl; R2 represents optionally substituted phenyl or diphenylmethyl; and m is 0, 1, or 2.

16. The compound of claim 1, wherein R represents independently for each occurrence H; R1 represents 4-chlorophenyl; R2 represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl; and m is 0, 1, or 2.

17. The compound of claim 1, wherein R represents independently for each occurrence H; R1 represents optionally substituted phenyl; R2 represents optionally substituted phenyl or diphenylmethyl; m is 0, 1, or 2; and n is 1.

18. The compound of claim 1, wherein R represents independently for each occurrence H; R1 represents 4-chlorophenyl; R2 represents 2-methoxyphenyl, 2-trifluoromethoxyphenyl, 2-isopropoxyphenyl, 2-fluorophenyl, 4-fluorophenyl, 2-chlorophenyl, 3-chlorophenyl, or di(4-fluorophenyl)methyl; m is 0, 1, or 2; and n is 1.

19. The compound of claim 1, wherein said compound is a single stereoisomer.

20. A formulation, comprising a compound of claim 1; and a pharmaceutically acceptable excipient.